United States Patent
Sugita et al.

(10) Patent No.: US 7,189,845 B2
(45) Date of Patent: Mar. 13, 2007

(54) METHOD FOR PRODUCING ε-CAPROLACTAM

(75) Inventors: Keisuke Sugita, Niihama (JP); Masaru Kitamura, Niihama (JP); Masahiro Hoshino, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/088,874

(22) Filed: Mar. 25, 2005

(65) Prior Publication Data

US 2005/0245740 A1    Nov. 3, 2005

(30) Foreign Application Priority Data

Mar. 30, 2004    (JP) .............................. 2004-098506

(51) Int. Cl.
*C07D 201/04* (2006.01)
(52) U.S. Cl. ....................... 540/535; 540/536
(58) Field of Classification Search ................ 540/535, 540/536
See application file for complete search history.

(56) References Cited

U.S. PATENT DOCUMENTS

| 4,155,876 A | 5/1979 | Danziger et al. |
| 6,265,574 B1 | 7/2001 | Kitamura et al. |

FOREIGN PATENT DOCUMENTS

| EP | 0 380 364 A2 | 8/1990 |
| EP | 0 388 070 A1 | 9/1990 |
| EP | 0 544 530 A1 | 6/1993 |
| EP | 0 544 531 A1 | 6/1993 |
| EP | 1 028 108 A1 | 8/2000 |
| JP | 53-35691 | 4/1978 |
| JP | 2000-229939 A | 8/2000 |
| WO | WO-00/04994 A1 | 2/2000 |

OTHER PUBLICATIONS

JP 2003236394 (machine translation), Aug. 26, 2003.*
English language abstract of JP 2003 236394 A (Aug. 26, 2003).
English language abstract of JP 06 107627 A (Apr. 19, 1994).

* cited by examiner

*Primary Examiner*—Bruck Kifle
(74) *Attorney, Agent, or Firm*—Birch, Stewart, Kolasch & Birch, LLP

(57) ABSTRACT

The invention provides a method for producing ε-caprolactam comprising the steps of: a reaction process which subjects cyclohexanone oxime to a Beckmann rearrangement reaction in the presence of a solid catalyst; and a catalyst regeneration process which regenerates the solid catalyst used in the reaction process by heat treatment under an atmosphere comprising an oxygen-containing gas, wherein the solid catalyst heat-treated in the catalyst regeneration process is used in the reaction process, the carbon contents in the solid catalyst in the reaction process and the catalyst regeneration process are maintained in a range of 0.5 to 2% by weight, and the nitrogen contents in the solid catalyst in the reaction process and the catalyst regeneration process are maintained in a range of 0.01 to 0.2% by weight.

According to the invention, ε-caprolactam can be produced in a high production yield for a long period of time by enhancing persistence of the catalytic activity for producing ε-caprolactam.

2 Claims, No Drawings

METHOD FOR PRODUCING ε-CAPROLACTAM

BACKGROUND OF THE INVENTION

1. Field of the Invention

The invention relates to a method for producing ε-caprolactam from cyclohexanone oxime.

2. Description of the Related Art

One of the known methods for producing ε-caprolactam is to subject cyclohexanone oxime to a Beckmann rearrangement reaction in the presence of a solid catalyst. However, it is a problem of this method that the catalytic activity decreases with time due to adhesion of a so-called coke component (carbonaceous substance) to the catalyst. Consequently, in a proposed method for producing ε-caprolactam, the solid catalyst is regenerated and reused by combining the reaction process with a catalyst regeneration process for recovering the catalytic activity.

For example, Japanese Patent Application Laid-Open (JP-A) No. 53-35691 has proposed a method for producing ε-caprolactam comprising a reaction process using a boric acid catalyst supported on carbon by a fluidized bed system and a catalyst regeneration process for heat-treating the catalyst at 400 to 700° C. using air, wherein a part of the catalyst taken out of a reactor is introduced into a regenerator so that the difference of the organically-bound nitrogen content in the catalyst before and after regeneration, which is called as a differential organic nitrogen content, is maintained in a range of 0.8 to 2% by weight, and the regenerated catalyst is returned into the reactor.

JP-A No. 2000-229939 has proposed a method for producing ε-caprolactam comprising a reaction process using a solid catalyst other than the boric acid catalyst in the fluidized bed system and a catalyst regeneration process for heat-treating the catalyst at a high temperature using an oxygen-containing gas, wherein the catalyst is continuously or intermittently taken out of the reactor and introduced into a regenerator, and the nitrogen content in the regenerated catalyst is controlled in a range of 10 to 2500 ppm before returning the regenerated catalyst to the reactor.

However, since persistence of catalytic activity is not always sufficient in these conventional methods, it was a problem that the conversion of cyclohexanone oxime and selectivity of ε-caprolactam decrease during long term reactions.

SUMMARY OF THE INVENTION

Accordingly, it is an object of the invention to provide a method for producing ε-caprolactam with a high production yield for a long period of time by controlling the reaction process and catalyst regeneration process so that persistence of the catalytic activity is enhanced.

The invention provides a method for producing ε-caprolactam comprising the steps of: a reaction process which subjects cyclohexanone oxime to a Beckmann rearrangement reaction in the presence of a solid catalyst; and a catalyst regeneration process which regenerates the solid catalyst used in the reaction process by heat treatment under an atmosphere comprising an oxygen-containing gas, wherein the solid catalyst heat-treated in the catalyst regeneration process is used in the reaction process, the carbon contents in the solid catalyst in the reaction process and the catalyst regeneration process are maintained in a range of 0.5 to 2% by weight, and the nitrogen contents in the solid catalyst in the reaction process and the catalyst regeneration process are maintained in a range of 0.01 to 0.2% by weight.

According to the invention, ε-caprolactam can be produced in a high production yield for a long period of time by enhancing persistence of the catalytic activity for producing ε-caprolactam.

DESCRIPTION OF THE PREFERRED EXAMPLES

The method for producing ε-caprolactam according to the invention comprises the steps of: a reaction process which subjects cyclohexanone oxime to a Beckmann rearrangement reaction in the presence of a solid catalyst, and a catalyst regeneration process which regenerates the solid catalyst used in the reaction process by heat treatment under an atmosphere comprising an oxygen-containing gas. Then, the solid catalyst heat-treated in the regeneration process is reused in the reaction process.

While a boric acid catalyst, silica-alumina catalyst, phosphoric acid catalyst, composite metal oxide catalyst and zeolite catalyst have been proposed as the solid catalyst for the Beckman rearrangement reaction used in the reaction process, the zeolite catalyst is preferable among them, a pentasil zeolite is more preferable, and MFI zeolite is particularly preferable.

The zeolite catalyst may be crystalline silica having a frame substantially consisting of only silicon and oxygen, or a crystalline metallosilicate containing other elements constituting the frame. Examples of the elements other than silicon and oxygen contained in the crystalline metallosilicate include Be, B, Al, Ti, V, Cr, Fe, Co, Ni, Cu, Zn, Ga, Ge, Zr, Nb, Sb, La, Hf and Bi. At least two of them may be contained in the crystalline metallosilicate. The atomic ratio of silicon relative to each of these elements is usually 5 or more, preferably 50 or more, and more preferably 500 or more. The atomic ratio can be measured by an atomic absorption method and a fluorescent X-ray method.

The zeolite catalyst can be favorably prepared by following steps. A hydrothermal synthesis is performed by using a silicon compound, quaternary ammonium compound, water and, if necessary, metal compound as starting materials. Then, the crystal obtained is dried and calcined, and is treated by allowing the crystal to contact ammonia or ammonium salts followed by drying.

The particle diameter of the solid catalyst is preferably 0.001 to 5 mm, more preferably 0.01 to 3 mm. The solid catalyst may be used as a molded body substantially composed of only the catalyst components, or a catalyst components supported on a carrier.

The Beckmann rearrangement reaction of cyclohexanone oxime using the solid catalyst may be carried out by a fixed bed system, fluidized bed system or moving bed system, and the reaction temperature is usually 250 to 500° C., preferably 300 to 450° C. The reaction pressure is usually 0.005 to 0.5 MPa, preferably 0.005 to 0.2 MPa. The feed rate (kg/h) of cyclohexanone oxime as the starting material per 1 kg of the catalyst, or the space velocity WHSV ($h^{-1}$) of cyclohexanone oxime as the starting material, is usually 0.1 to 20 $h^{-1}$, preferably 0.2 to 10 $h^{-1}$.

Cyclohexanone oxime may be introduced, alone or together with an inert gas such as nitrogen, argon or carbon dioxide, into a reaction system. Other effective methods comprise adding ether together as disclosed in JP-A No. 2-25086, adding a lower alcohol together as disclosed in JP-A No. 2-275850, adding an alcohol and/or ether and water together as disclosed in JP-A No. 5-201965, adding ammonia together as disclosed in JP-A No. 5-201966, and adding methylamine together as disclosed in JP-A No. 6-107627. Thus, a material gas containing cyclohexanone oxime may be prepared to be used.

The catalytic activity gradually decreases, or the conversion ratio of cyclohexanone oxime gradually decreases, in the Beckmann rearrangement reaction of cyclohexanone oxime in the presence of the solid catalyst usually with a lapse of the reaction time or, in other words, with an increase of a total amount of cyclohexanone oxime processed per unit weight of the catalyst, due to gradual adhesion of so-called coke components on the solid catalyst caused by polymerization of cyclohexanone oxime or $\epsilon$-caprolactam. Accordingly, a catalyst regeneration process comprising heat-treatment in an oxygen-containing atmosphere is provided in order to recover the catalytic activity by removing the coke components from the solid catalyst for.

While air is usually suitable as the oxygen-containing gas used in the catalyst regeneration process, an air or an oxygen gas diluted with an inert gas such as nitrogen, argon and carbon dioxide may be also used. The concentration of oxygen in the oxygen-containing gas is usually 1 to 30% by volume, preferably 5 to 25% by volume. The heat treatment temperature in the catalyst regeneration process is usually 200 to 600° C., preferably 200 to 400° C.

However, reduction of the activity of the solid catalyst is not completely avoided even by providing the above catalyst regeneration process, and the conversion of cyclohexanone oxime or selectivity of $\epsilon$-caprolactam may decrease during long term uses. Accordingly, in the invention, in order to suppress the activity of the solid catalyst from decreasing, or in order to enhance persistence of the performance of the solid catalyst, the carbon content in the solid catalyst in the reaction process and the catalyst regeneration process is controlled within a range of 0.5 to 2%, preferably 0.7 to 1.8%, by weight and the nitrogen content in the solid catalyst in the reaction process and the catalyst regeneration process is controlled within a range of 0.01 to 0.2%, preferably 0.01 to 0.15%, by weight. Persistence of the performance of the catalyst may be enhanced by maintaining the respective amounts of the carbon components and nitrogen components, which are ascribed to coke components adhered on the solid catalyst, in prescribed ranges both in the reaction process and catalyst regeneration process. The respective contents of carbon and nitrogen in the catalyst may be below the ranges above immediately after charging a freshly produced catalyst.

The contents of carbon and nitrogen can be determined by measuring the amounts of total carbon (TC) and total nitrogen (TN) in the solid catalyst, respectively. Particularly, a prescribed amount of the solid catalyst is oxidized with oxygen gas, and the amounts of carbon oxides and nitrogen oxides are measured by gas chromatography or IR spectroscopy. The amount of the total carbon oxides is converted into an amount of the carbon atoms while the amount of the total nitrogen oxides is converted into an amount of the nitrogen atoms, and they are divided by the amount of the solid catalyst, respectively, to determine TC and TN.

The contents of carbon and nitrogen in the solid catalyst usually increase in the reaction process and decrease in the catalyst regeneration process. Therefore, the carbon content in the solid catalyst is maintained to be 2% by weight or less, preferably 1.8% by weight or less, and the nitrogen content in the solid catalyst is maintained to be 0.2% by weight or less, preferably 0.15% by weight or less, so as to avoid coke components from adhering too much on the solid catalyst in the reaction process. On the other hand, the carbon content and nitrogen content in the solid catalyst are maintained to be 0.5% by weight or more, preferably 0.7% by weight or more, and 0.01% by weight or more, respectively, in the catalyst regeneration process so as to avoid coke components adhered on the solid catalyst from being too much removed.

In a preferably employed process using the fixed bed catalyst, the material gas containing cyclohexanone oxime is allowed to react by feeding it to a reactor filled with the solid catalyst followed by halting feed of the material gas, the solid catalyst is heat-treated with feeding an oxygen-containing gas, and these reactions and heat-treatment steps are repeated in this order. In other words, it is preferable that, the material gas and an oxygen-containing gas are alternately supplied to the reactor filled with the solid catalyst to repeat the reaction process and the catalyst regeneration process. In this embodiment, since the carbon content and nitrogen content gradually increase in the reaction process, it is suitable that the feed gas is switched from the material gas to the oxygen-containing gas before the carbon content exceeds 2%, preferably 1.8%, by weight and the nitrogen content exceeds 0.2%, preferably 0.15%, by weight. On the other hand, since the carbon content and nitrogen content gradually decrease in the catalyst regeneration process, it is suitable that the feed gas is switched from the oxygen-containing gas to the material gas before the carbon content decreases below 0.5%, preferably 0.7%, by weight and the nitrogen content decreases below 0.01% by weight. When using fixed bed system, said carbon content and nitrogen content may be measured with sampling a necessary amount of the solid catalyst properly in the interval between the processes. But such a sampling action may cause the reaction condition to be fluctuated, and if such a situation is not preferred, several test runs, which are terminated on sampling the solid catalyst, may be proceeded to determine reaction conditions which satisfy the conditions involved in the present invention, and actual production may be proceeded under the determined reaction conditions.

In a preferably employed process using the fluidized bed catalyst, the solid catalyst is continuously or intermittently taken out of the reactor while the material gas containing cyclohexanone oxime is allowed to react by feeding it to the reactor in which the solid catalyst is flowing, and the solid catalyst is introduced into a catalyst regenerator for heat-treatment in an atmosphere of the oxygen-containing gas followed by returning the catalyst to the reactor. In other words, it is preferable that the solid catalyst is circulated between the reactor and the catalyst regenerator so that the reaction process and the catalyst regeneration process are concomitantly proceeded. In a preferably employed process using the moving bed catalyst, the solid catalyst is being introduced into the reactor while the material gas containing cyclohexanone oxime is allowed to react by feeding it to a reactor, the catalyst discharged from the reactor is introduced into a catalyst regenerator, and returned to the reactor again after heat-treated in an atmosphere of the oxygen-containing gas. In other words, it is preferable that the solid catalyst is circulated between the reactor and the catalyst regenerator so that the reaction process and the catalyst regeneration process are concomitantly proceeded. Since the carbon content and nitrogen content in the solid catalyst increase as the residence time of the solid catalyst in the reactor is prolonged in the reaction process, it is suitable that the residence time is appropriately shortened so that the carbon content does not exceed 2%, preferably 1.8%, by weight and the nitrogen content does not exceed 0.2%, preferably 0.15%, by weight. On the other hand, since the carbon content and nitrogen content in the solid catalyst decrease as the residence time of the solid catalyst in the regenerator is prolonged or as the heat treatment temperature is higher in the catalyst regeneration process, it is suitable that the residence time is appropriately shortened or the heat treatment temperature is appropriately lowered so that the carbon content is not reduced below 0.5%, preferably 0.7%, by weight and the nitrogen content is not reduced below 0.01% by weight. A necessary amount of the solid catalyst may be sampled when the solid catalyst is transferred between the reactor and the catalyst regenerator in case of fluidized bed system or moving bed system to measure said carbon content and nitrogen content.

In a method for separating ε-caprolactam from the reaction mixture obtained in the reaction process, for example, a reaction product gas is condensed by cooling, and the condensed product is isolated, by extraction, distillation and crystallization.

EXAMPLES

While examples of the invention are shown below, the invention is by no means restricted to these examples. The carbon content and nitrogen content in the solid catalyst were assayed using an NCH quantitative analyzer (trade name; Sumigraph NCH-21 (based on combustion by circulating oxygen, detected by TCD-GC), manufactured by Sumika Chemical Analysis Service. Ltd.). Cyclohexanone oxime and ε-caprolactam were analyzed by gas chromatography, and the conversion of cyclohexanone oxime and selectivity of ε-caprolactam were calculated by the following equations:

Conversion (%) of cyclohexanone oxime=$[(X-Y)/X]\times 100$

Selectivity (%) of ε-caprolactam=$[Z/(X-Y)]\times 100$ where X is a mole number of supplied cyclohexanone oxime, Y is a mole number of unreacted cyclohexanone oxime, and Z is a mole number of ε-caprolactam formed.

Example 1

Crystalline silica having an MFI structure with a particle diameter of 0.3 mm or less was used as a catalyst, and a catalyst layer was formed by filling 0.375 g of the catalyst in a quartz glass reactor tube with an inner diameter of 1 cm. The reactor tube was subjected to pre-heat treatment for 1 hour at a temperature of 340° C. with allowing nitrogen to flow through into the reactor tube at a flow rate of 4.2 L/h. Then, the reactor tube temperature was raised to 380° C. while the flow rate of nitrogen is kept at 4.2 L/h. A mixture of cyclohexanone oxime and methanol in a weight ratio of 1/1.8 was fed to the reactor tube at a flow rate of 8.4 g/h (WHSV of cyclohexanone oxime=8 h$^{-1}$), and the reaction was continued for 1 hour at the same temperature.

Feed of the mixture of cyclohexanone oxime and methanol was halted thereafter, and the temperature of the reactor tube was lowered to 340° C. at a nitrogen flow rate of 4.2 L/h. Then, the feed gas was switched from nitrogen to air, and the catalyst was heat-treated for 0.5 hour with feeding air at a flow rate of 5 L/h at the same temperature. Subsequently, air is switched to nitrogen at a flow rate of 4.2 L/h.

A series of operations from the reaction to the heat treatment was repeated. The carbon content and nitrogen content in the solid catalyst after the 21 times reactions were 1.77% by weight and 0.13% by weight, respectively. The series of operations from the reaction to the heat treatment above-mentioned was repeated again, the carbon content and nitrogen content in the solid catalyst after the 21 times heat treatments were 0.76% by weight and 0.011% by weight, respectively. When the series of operations from the reaction to the heat treatment above-mentioned was repeated more than 120 hours, the conversion of cyclohexanone oxime and selectivity of ε-caprolactam after 21 hours' total reaction time (measured at 1 hour after the 21-st reaction) were 99.9% and 96.9%, respectively, while the conversion of cyclohexanone oxime and selectivity of ε-caprolactam after 120 hours' total reaction time (measured at the start of the 121-st reaction) were also 99.9% and 96.9%, respectively.

Comparative Example 1

Crystalline silica having an MFI structure with a particle diameter of 0.3 mm or less was used as a catalyst, and a catalyst layer was formed by filling 0.375 g of the catalyst in a quartz glass reactor tube with an inner diameter of 1 cm. The reactor tube was subjected to pre-heat treatment for 1 hour at a temperature of 340° C. with allowing nitrogen to flow through into the reactor tube at a flow rate of 4.2 L/h. Then, the reactor tube temperature was raised to 380° C. while the flow rate of nitrogen is kept at 4.2 L/h. A mixture of cyclohexanone oxime and methanol in a weight ratio of 1/1.8 was fed to the reactor tube at a flow rate of 8.4 g/h (WHSV of cyclohexanone oxime=8 h$^{-1}$), and the reaction was continued for 20 hours at the same temperature.

Feed of the mixture of cyclohexanone oxime and methanol as halted thereafter, and the temperature of the reactor tube was lowered to 340° C. at a nitrogen flow rate of 4.2 L/h. Then, the feed gas was switched from nitrogen to air, and feeding air at a flow rate of 5 L/h the temperature of the reactor tube was raised from 340° C. to 500° C., and the catalyst was heat-treated for 20 hours at 500° C. Subsequently, air is switched to nitrogen at a flow rate of 4.2 L/h.

A series of operations from the reaction to the heat treatment was repeated. The carbon content and nitrogen content in the solid catalyst after the 2 times reactions were 2.28% by weight and 0.17% by weight, respectively. The series of operations from the reaction to the heat treatment above-mentioned was repeated again, the carbon content and nitrogen content in the solid catalyst after the 2 times heat treatments were 0.10% by weight and 0.002% by weight, respectively. When the series of operations from the reaction to the heat treatment above-mentioned was repeated more than 120 hours, the conversion of cyclohexanone oxime and selectivity of ε-caprolactam after 21 hours' total reaction time (measured at 1 hour after the second reaction) were 99.9% and 96.5%, respectively, while the conversion of cyclohexanone oxime and selectivity of ε-caprolactam after 120 hours' total reaction time (measured at the start of the seventh reaction) were 99.4% and 95.5%, respectively.

What is claimed is:

1. A method for producing ε-caprolactam comprising the steps of: a reaction process which subjects cyclohexanone oxime to a Beckmann rearrangement reaction in the presence of a solid catalyst; and a catalyst regeneration process which regenerates the solid catalyst used in the reaction process by heat treatment under an atmosphere comprising an oxygen-containing gas, wherein the solid catalyst heat-treated in the catalyst regeneration process is used in the reaction process, the carbon content in the solid catalyst in the reaction process and catalyst regeneration process is maintained in a range of 0.5 to 2% by weight, and the nitrogen content in the solid catalyst in the reaction process and catalyst regeneration process is maintained in a range of 0.01 to 0.2% by weight.

2. The method according to claim 1, wherein the solid catalyst is a zeolite catalyst.

* * * * *